US006221629B1

United States Patent
Marshall et al.

(10) Patent No.: US 6,221,629 B1
(45) Date of Patent: *Apr. 24, 2001

(54) EXPRESSION VECTORS AND PROCESS FOR PRODUCING HUMAN B CELL SURFACE MOLECULE RP105

(75) Inventors: Lisa A. Marshall, Wyndmoor; Amy K. Roshak, East Norriton, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/060,208

(22) Filed: Jan. 14, 1998

Related U.S. Application Data

(62) Division of application No. 08/730,771, filed on Oct. 16, 1996, now Pat. No. 5,780,609.
(60) Provisional application No. 60/005,642, filed on Oct. 19, 1995.

(51) Int. Cl.[7] .............................. C12N 15/63; C07H 21/04
(52) U.S. Cl. .................... 435/69.1; 435/71.1; 435/252.3; 435/320.1; 435/455; 435/471; 536/23.1; 536/23.5
(58) Field of Search .................................. 536/23.1, 23.5; 435/69.1, 455, 252.3

(56) References Cited

U.S. PATENT DOCUMENTS

| | | | |
|---|---|---|---|
| 5,155,218 | * | 10/1992 | Weinshank et al. . |
| 5,348,864 | * | 9/1994 | Barbacid . |
| 5,707,829 | * | 1/1998 | Jacobs et al. . |
| 5,780,609 | * | 7/1998 | Marshall et al. . |

FOREIGN PATENT DOCUMENTS

WO 97/07198   2/1997  (WO) .

OTHER PUBLICATIONS

Obernolte, R. et al., "The cDNA of a human lymphocity cyclic–AMP phosphodiesterase (PDE IV) reveals a multigene family", Gene vol. 129, pp. 239–247 (1993).

Wood, Jr., W.J. et al., "Isolation and Chromosomal Mapping of the Human Immunoglobulin Associated B29 Gene (IGB)", Genomics vol. 16, pp. 187–192 (1993).

Miyake et al., "RP105, A Novel B Cell Surface Molecule Implicated in B Cell Activation, Is a Member of the Leucine–Rich Repeat Protein Family", J. Immunol. vol. 154, pp. 3333–3334 (1995).

Miyake, K. et al., "Murine B Cell Proliferation and Protection from Apoptosis with an Antibody Against a 105kD Molecule: Unresponsiveness of X–linked Immunodeficient B Cells", J. Exp. Med., vol. 180, pp. 1217–1224 (1994).

* cited by examiner

*Primary Examiner*—Christina Y. Chan
*Assistant Examiner*—Phillip Gambel
(74) *Attorney, Agent, or Firm*—William T. Han; Ratner & Prestia; William T. King

(57) ABSTRACT

Nucleic acid molecules encoding a human B cell surface molecule are provided. Polypeptides and antibodies which bind to these polypeptides are also provided. In addition, methods of detecting mutated forms of the molecule are provided.

5 Claims, No Drawings

EXPRESSION VECTORS AND PROCESS FOR PRODUCING HUMAN B CELL SURFACE MOLECULE RP105

This application claims the benefit of U.S. Provisional Application No. 60/005,642, filed Oct. 19, 1995.

This application is a division of application Ser. No. 08/730,771, filed Oct. 16, 1996, now U.S. Pat. No. 5,780,609.

BACKGROUND OF THE INVENTION

Mature B cells comprise 10 to 15 percent of human peripheral blood lymphocytes, 50 percent of splenic lymphocytes, and approximately 10 percent of bone marrow lymphocytes. Mature B cells are derived from bone marrow precursor cells that arise continuously throughout life. B cells express on their surface intramembrane immunoglobulin (Ig) molecules that function as B cell antigen receptors in a complex of Ig-associated à and þ signaling molecules with intracellular signaling events. B cells also express surface receptors for the Fc region of IgG molecules as well as receptors for activated complement components. The primary function of B cells is to produce antibodies.

B cells undergo several selection steps during differentiation from immature cells to mature B cells or antibody-secreting cells. Only B cells which have undergone the selection process join the mature B cell pool and differentiate into antibody secreting cells upon stimulation. These selections allow for maintenance of a stable B cell pool without the production of autoreactive B cells which react to create an autoimmune response and efficient antibody production with adequate specificity and affinity. von Boehmer, H. Cell 1994 76:210; Liu et al. Immunol. Today 1992 13:17; Liu et al. Nature (Lond.) 1989 342:929. The selection steps involve apoptosis, survival or proliferation of B cells. A study in double transgenic mice revealed that apoptosis is important in the negative selection that destroys B cells bearing aberrant specificity against self-antigens. Hartley et al. Cell 1993 72:325. The autoantigen itself or the autoantigen in combination with other signals triggered apoptosis in these hazardous cells. In contrast, positive selection requires a condition where only cells receiving a signal are able to survive and grow. Otherwise, cells undergo apoptosis. In the germinal center, only cells bearing a surface immunoglobulin with sufficient affinity against an antigen are allowed to survive and grow. Liu et al. Immunol. Today 1992 13:17. In this situation, stimulatory signals such as the antigen itself or the CD40 ligand are shown to protect cells from apoptosis and induce survival or proliferation. Liu et al. Immunol. Today 1992 13:17; Liu et al. Nature (Lond.) 1989 342:929. Thus, apoptosis plays an essential role in the selection process. A signal that is capable of inducing or blocking apoptosis has been implicated as a pivotal system for selecting B cells.

Lymphocytes such as B cells are one of the most sensitive cells to immediate radiation induced damage. Anderson, R. E., and Warner, N. L. Adv. Immunol. 1976 24:215. Quiescent lymphocytes have been found to be more sensitive than actively cycling cells. The damaged cells are believed to undergo apoptosis. This process, which does not involve cell division, is sometimes referred to as interphase death. It has been hypothesized that lymphocyte signaling systems which are important in facilitating the B cell selection process are also related to cell death by irradiation.

Miyake et al. J. Exp. Med. 1994 180:1217–1224 disclose a monoclonal antibody, RP/14, that protects murine B cells from apoptosis induced by irradiation or dexamethasone. A molecule recognized by this antibody was found to be expressed on the murine B cells. This murine B cell surface molecule, referred to as RP105, has been further characterized. Miyake et al. J. Immunol. 1995 154:3333–3340. RP105 is a murine B cell antigen. It is monomeric, with a size of approximately 105 kDa. It is expressed on mature B cells, but not on either immature or pre-B cells. This antigen is believed to transmit a signal into murine B cells that results in protection from radiation or dexamethasone induced apoptosis.

The N-terminal amino acid sequence of the murine RP105 molecule has been determined. A cDNA clone was also isolated with a probe corresponding to the obtained amino acid sequence. DNA sequencing revealed that an encoded murine polypeptide is a type 1 transmembrane protein consisting of 641 amino acids in a mature form. Northern hybridization with the clone detected a transcript of approximately 3 kb. This transcript was found in mouse spleen, but not thymus, kidney, muscle, heart, brain or liver. Transfection of the clone into a pro-B cell line resulted in the expression of RP105.

A computer search showed similarity of murine RP105 to a number of molecules including decorin and biglycan, which are human proteoglycans in extracellular tissue; the Drosophila toll, tartan, connectin, chaoptin and slit proteins (which are responsible for dorsal/ventral polarity, epidermal/subepidermal structure, target recognition of a subset of motor neurons, photoreceptor morphogenesis and pathway finding by commissural axons during embryogenesis); and the à-subunit of platelet glycoprotein Ib (involved in platelet adhesion to vascular endothelial cells). Miyake et al. J. Immunol. 1995 154:3333–3340. The property shared by murine RP105 and these molecules is tandem repeats of a leucine-rich motif (LRM) These repeated motifs are observed in members of the leucine-rich repeat protein family and have been implicated in protein-protein interactions such as cell adhesion or receptor-ligand binding. The murine RP105 molecule has 22 tandem repeats of a leucine-rich motif, as well as amino and carboxyl flanking regions that are characteristically conserved among members of this family. Thus, murine RP105 is believed to be a member of the leucine-rich repeat family and the first one that is expressed specifically on mature B cells.

A human gene encoding a novel human B cell surface molecule has now been found.

SUMMARY OF THE INVENTION

An object of the present invention is to provide isolated nucleic acid molecules encoding a novel human B cell surface molecule human including mRNAs, DNAs, cDNAs, genomic DNAs as well as analogs and biologically active and diagnostically or therapeutically useful fragments thereof.

Another object of the present invention is to provide a polypeptide which is a novel human B cell surface molecule, as well as biologically active and diagnostically or therapeutically useful fragments, analogs and derivatives thereof.

Another object of the present invention is to provide antibodies or receptor bodies against this polypeptide.

Another object of the present invention is to provide a process for producing this polypeptide by recombinant techniques comprising culturing recombinant prokaryotic and/or eukaryotic host cells, containing a human nucleic acid sequence for the novel human B cell surface molecule under conditions promoting expression of this polypeptide and subsequent recovery of this polypeptide.

These and other aspects of the present invention should be apparent to those skilled in the art from the teachings herein.

DETAILED DESCRIPTION OF THE INVENTION

A gene encoding an antigen on human B cells involved in B cell proliferation and protection from dexamethasone- and irradiation-induced apoptosis has now been found. The nucleotide sequence of this gene has been determined and is provided as SEQ ID NO: 1. A plasmid containing the cDNA clone for this novel human B cell surface molecule was deposited as ATCC Deposit No. 69902.

The cDNA for this novel human B cell surface molecule is 2775 bp in length. It is 71.9% identical to murine RP105 at the nucleotide level. Nucleotide 140 through 2092 of the cDNA encode an open reading frame of 651 amino acids, similar in size to mouse RP105 (662 amino acids). The translated polypeptide from the open reading frame of the human cDNA is 73.1% identical to murine RP105 with the leucine-rich repeats being conserved.

The present invention further relates to polypeptides encoded by the cDNA clone of this human B cell surface molecule as well as fragments, analogs and derivatives of such polypeptides. The terms "fragment," "derivative" and "analog" when referring to the polypeptides encoded by the deposited cDNA, means a polypeptide which retains essentially the same biological function or activity. Thus, an analog includes a proprotein which can be activated by cleavage of the proprotein portion to produce an active mature polypeptide. The polypeptide of the present invention may be a recombinant polypeptide, a natural polypeptide or a synthetic polypeptide, preferably a recombinant polypeptide.

The fragment, derivative or analog of the polypeptides encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein. The polypeptides and polynucleotides of the present invention are preferably provided in an isolated form, and preferably are purified to homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include the cDNA clone of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The cDNA clone of the present invention may be employed for producing polypeptides by recombinant techniques. Thus, for example, the cDNA clone may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate clone may be inserted into the vector by a variety of procedures. In general, the cDNA sequence is inserted into an appropriate restriction endonuclease site(s) by procedures known in the art. Such procedures and others are deemed to be within the scope of those skilled in the art.

The cDNA sequence in the expression vector is operatively linked to an appropriate expression control sequence (s) (promoter) to direct MRNA synthesis. As representative examples of such promoters, there may be mentioned: LTR or SV40 promoter, the *E. coli*, lac or trp, the phage lambda PL promoter and other promoters known to control expression of genes in prokalyotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate cDNA clone as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising the cDNA sequence. The constructs comprise a vector, such as a plasmid or viral vector, into which the clone has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host. In addition, a complete mammalian transcription unit and a selectable marker can be inserted into a prokaryotic plasmid. The resulting vector is then amplified in bacteria before being transfected into cultured mammalian cells. Examples of vectors of this type include pTK2, pHyg and pRSVneo.

Promoter regions can be selected from any desired gene using CAT (chloramphenicol acetyl transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be performed by calcium phosphate transfection, DEAE-dextran mediated transfection, Polybrene, protoplast fusion, liposomes, direct microinjection into the nuclei, scrape loading or electroporation.

The constructs in host cells can be used in a conventional manner to produce the gene product encoded by the cDNA clone. Alternatively, polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention both in vitro and in vivo. Appropriate cloning and expression vectors for use with prokaryotic and eukaryotic hosts are described by Sambrook et al., "Molecular Cloning: A Laboratory Manual", Second Edition, Cold Spring Harbor, N.Y., (1989), the disclosure of which is hereby incorporated by reference.

Transcription of DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), à-factor, acid phosphatase, or heat shock proteins, among others. The heterologous structural sequence is assembled in appropriate phase with translation initiation and termination sequences, and preferably, a leader sequence capable of directing secretion of translated protein into the piroplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable and nonselectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice. In addition, a complete mammalian transcription unit and a selectable marker can be inserted into a prokaryotic plasmid. The resulting vector is then amplified in bacteria before being transfected into cultured mammalian cells.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include COS and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

Larger quantities of protein can be obtained from cell lines carrying amplified copies of the gene of interest. In this method, the gene is attached to a segment of DNA that carries a selectable marker and transfected into the cells, or are cotransfected into the cells. Sublines are then selected in which the number of copies of the gene are greatly amplified. There are a wide variety of selectable markers available in the art. For example, the dhfr gene is extensively used for coamplification. After several months of growth in progressively increasing concentrations of methotrexate, cell lines can be obtained that carry up to 1000 copies of the dhfr gene.

The polypeptide can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Because of the integral role of the B cell surface molecule in the signaling events involved in the selection of B cells which survive and proliferate, mutations in this molecule may result in abnormal cellular signals thus causing an abnormal B cell selection and possibly abnormal antibody production. Accordingly, the cDNAs of the present invention may be used as a diagnostic in the detection of mutated forms of this molecule. Such detection will allow a diagnosis of an abnormal cellular response resulting from these mutations.

Individuals carrying mutations in the human gene encoding the antigen may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al. Nature, 324:163–166 (1986)) prior to analysis. RNA or cDNA may also be used for the same purpose. As an example, PCR primers complementary to the nucleic acid encoding the gene can be used to identify and analyze mutations. For example, deletions and insertions can be detected by a change in size of the amplified product in comparison to the normal genotype. Point mutations can be identified by hybridizing amplified DNA to radiolabeled antigen or alternatively, radiolabeled antigen antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al. Science, 230:1242 (1985)).

Sequence changes at specific locations may also be revealed by nuclease protection assays, such as RNase and S1 protection or the chemical cleavage method (e.g., Cotton et al. PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. In addition to more conventional gel-electrophoresis and DNA sequencing, mutations can also be detected by in situ analysis.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against polypeptides encoded by the cDNA sequence of the present invention or a fragment thereof can be obtained by direct injection of the polypeptides into an animal or by administering the polypeptides to an animal, preferably a nonhuman. The cDNA clone may also be used in the development of gene vaccines which have been shown to been an effective method for eliciting an immune response in a host. Tang et al. Nature 1992 356:152–154. Gene vaccines represent a relatively new approach for producing antibodies in a host. Immunization with gene vaccines has been shown to result in host cells taking up and expressing an inoculated DNA. Antibodies are then produced against the newly expressed protein. Vaccine DNAs can be constructed by creating plasmids which express a polypeptide of the present invention. Such vaccines can then be administered intramuscularly, intravenously, intradermally or subcutaneously to a host. Fynan et al. Proc. Nat'l Acad. Sci. USA 1993 90:11478–11482.

Antibodies raised by these methods will then bind the polypeptides of the present invention. In this manner, even a sequence encoding only a fragment of the polypeptides can be used to generate antibodies binding the whole native polypeptide. Such antibodies can then be used therapeutically to protect human B cells from apoptosis resulting from dexamethasone treatment and irradiation.

For preparation of monoclonal antibodies, any technique which provides antibodies produced by continuous cell line cultures can be used. Examples include the hybridoma technique (Kohler and Milstein Nature (1975)

256:495–497), the trioma technique, the human B-cell hybridoma technique (Kozbor et al. Immunology Today (1983) 4:72), and the EBV-hybridoma technique to produce human monoclonal antibodies (Cole et al., 1985, in "Monoclonal Antibodies and Cancer Therapy", Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The polypeptides of the present invention can also be used in the development of receptor bodies, also referred to as immunoadhesins, which are antibody-like molecules comprising an immunoglobulin like domain of a membrane protein fused to the constant region of antibody heavy and light chains. Methods for developing these molecules are known in the art as exemplified by Capon et al. Nature 1989337:525–531.

The following nonlimiting examples are provided to further illustrate the present invention.

EXAMPLES

Example 1

Isolation and Analysis of cDNA clone cDNA libraries were constructed by directional cloning of cDNA from each tissue into the Stratagene UniZapXR lambdaphage vector (Stratagene, La Jolla, Calif.). Primary libraries were immediately amplified. The pBluescriptSK+ plasmid (contained within the Unizap phage) was excised by co-infection of Stratagene XL1-Blue MRF' cells with helper phage and an aliquot of the amplified library. This resulting phagemid stock was used to infect Stratagene SOLR cells which were subsequently plated on LB+ ampicillin plates. DNA was made from individual colonies, sequenced on an ABI 373a automated sequencer, and the resulting sequence analyzed by the BLAST program. The insert is in the EcoR1(5')/Xho1(3') sites of BluescriptSK+.

What is claimed is:

1. An expression vector comprising a polynucleotide expressing the polypeptide encoded by the sequence set forth in SEQ ID NO:1 when said expression system is present in a compatible host cell.

2. An expression vector comprising a polynucleotide capable of producing a polypeptide encoded by the sequence set forth in SEQ ID NO:1 when said expression vector is present in a compatible host cell.

3. A process for producing a recombinant host cell comprising transforming or transfecting a cell with the expression vector of claim 1 such that the host cell, under appropriate culture conditions, produces a polypeptide encoded by the sequence of SEQ ID NO: 1.

4. A recombinant host cell produced by the process of claim 3.

5. A process for producing a polypeptide comprising culturing a recombinant host cell of claim 4 under conditions sufficient for the production of said polypeptide and recovering the polypeptide from the culture.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 2775 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
TTAGCAAGTC GACTTATCCT CACTAAAGGG AACAAAAGCT GGAGCTCCAC CGCGGTGGCG      60

GCCGCTCTAG AACTAGTGGA TCCCCCGGGC TGCAGGAATT CGGCACGAGG GTAAACCCAC     120

CAAGCAATCC TAGCCTGTGA TGGCGTTTGA CGTCAGCTGC TTCTTTTGGG TGGTGCTGTT     180

TTCTGCCGGC TGTAAAGTCA TCACCTCCTG GGATCAGATG TGCATTGAGA AAGAAGCCAA     240

CAAAACATAT AACTGTGAAA ATTTAGGTCT CAGTGAAATC CCTGACACTC TACCAAACAC     300

AACAGAATTT TTGGAATTCA GCTTTAATTT TTTGCCTACA ATTCACAATA GAACCTTCAG     360

CAGACTCATG AATCTTACCT TTTTGGATTT AACTAGGTGC CAGATTAACT GGATACATGA     420

AGACACTTTT CAAAGCCATC ATCAATTAAG CACACTTGTG TTAACTGGAA ATCCCCTGAT     480

ATTCATGGCA GAAACATCGC TTAATGGGCC CAAGTCACTG AAGCATCTTT TCTTAATCCA     540

AACGGGAATA TCCAATCTCG AGTTTATTCC AGTGCACAAT CTGGAAAACT TGGAAAGCTT     600

GTATCTTGGA AGCAACCATA TTTCCTCCAT TAAGTTCCCC AAAGACTTCC CAGCACGGAA     660

TCTGAAAGTA CTGGATTTTC AGAATAATGC TATACACTAC ATCTCTAGAG AAGACATGAG     720
```

-continued

```
GTCTCTGGAG CAGGCCATCA ACCTAAGCCT GAACTTCAAT GGCAATAATG TTAAAGGTAT      780
TGAGCTTGGG GCTTTTGATT CAACGGTCTT CCAAAGTTTG AACTTTGGAG GAACTCCAAA      840
TTTGTCTGTT ATATTCAATG GTCTGCAGAA CTCTACTACT CAGCCTCTCT GGCTGGGAAC      900
ATTTGAGGAC ATTGATGACG AAGATATTAG TTCAGCCATG CTCAAGGGAC TCTGTGAAAT      960
GTCTGTTGAG AGCCTCAACC TGCAGGAACA CCGCTTCTCT GACATCTCAT CCACCACATT     1020
TCAGTGCTTC ACCCAACTCC AAGAATTGGA TCTGACAGCA ACTCACTTGA AAGGGTTACC     1080
CTCTGGGATG AAGGGTCTGA ACTTGCTCAA GAAATTAGTT CTCAGTGTAA ATCATTTCGA     1140
TCAATTGTGT CAAATCAGTG CTGCCAATTT CCCCTCCCTT ACACACCTCT ACATCAGAGG     1200
CAACGTGAAG AAACTTCACC TTGGTGTTGG CTGCTTGGAG AAACTAGGAA ACCTTCAGAC     1260
ACTTGATTTA AGCCATAATG ACATAGAGGC TTCTGACTGC TGCAGTCTGC AACTCAAAAA     1320
CCTGTCCCAC TTGCAAACCT TAAACCTGAG CCACAATGAG CCTCTTGGTC TCCAGAGTCA     1380
GGCATTCAAA GAATGTCCTC AGCTAGAACT CCTCGATTTG GCATTTACCC GCTTACACAT     1440
TAATGCTCCA CAAAGTCCCT TCCAAAACCT CCATTTCCTT CAGGTTCTGA ATCTCACTTA     1500
CTGCTTCCTT GATACCAGCA ATCAGCATCT TCTAGCAGGC CTACCAGTTC TCCGGCATCT     1560
CAACTTAAAA GGGAATCACT TTCAAGATGG GACTATCACG AAGACCAACC TACTTCAGAC     1620
CGTGGGCAGC TTGGAGGTTC TGATTTTGTC CTCTTGTGGT CTCCTCTCTA TAGACCAGCA     1680
AGCATTCCAC AGCTTGGGAA AAATGAGCCA TGTAGACTTA AGCCACAACA GCCTGACATG     1740
CGACAGCATT GATTCTCTTA GCCATCTTAA GGGAATCTAC CTCAATCTGG CTGCCAACAG     1800
CATTAACATC ATCTCACCCC GTCTCCTCCC TATCTTGTCC CAGCAGAGCA CCATTAATTT     1860
AAGTCATAAC CCCCTGGACT GCACTTGCTC GAATATTCAT TTCTTAACAT GGTACAAAGA     1920
AAACCTGCAC AAACTTGAAG GCTCGGAGGA GACCACGTGT GCAAACCCGC CATCTCTAAG     1980
GGGAGTTAAG CTATCTGATG TCAAGCTTTC CTGTGGGATT ACAGCCATAG GCATTTTCTT     2040
TCTCATAGTA TTTCTATTAT TGTTGGCTAT TCTGCTATTT TTTTGCAGTT AAATACCTTC     2100
TCAGGTGGAA ATACCAACAC ATTTAGTGCT GAAGGTTTCC AGAGAAAGCA AATAAGTGTG     2160
CTTAGCAAAA TTGCTCTAAG TGAAAGAACT GTCATCTGCT GGTGACCAGA CCAGACTTTT     2220
CAGATTGCTT CCTGGAACTG GGCAGGGACT CACTGTGCTT TTCTGAGCTT CTTACTCCTG     2280
TGAGTCCCAG AGCTAAAGAA CCTTCTAGGC AAGTACACCG AATGACTCAG TCCAGAGGGT     2340
CAGATGCTGC TGTGAGAGGC ACAGAGCCCT TTCCGCATGT GGAAGAGTGG GAGGAAGCAG     2400
AGGGAGGGAC TGGGCAGGGA CTGCCGGCCC CGGAGTCTCC CACAGGGAGG CCATTCCCCT     2460
TCTACTCACC GACATCCCTC CCAGCACCAC ACACCCCGCC CCTGAAAGGA GATCATCAGC     2520
CCCCACAATT TGTCAGAGCT GAAGCCAGCC CACTACCCAC CCCCACTACA GCATTGTGCT     2580
TGGGTCTGGG TTCTCAGTAA TGTAGCCATT TGAGAAACTT ACTTGGGGAC AAAGTCTCAA     2640
TCCTTATTTT AAATGAAAAA AGAAAAGAAA AGCATAATAA ATTTAAAAGA AAAGGCTGAG     2700
AAAAAAAAAA AAAAAAAACT CGAGGGGGGC CCGTACCCAA TTCGCACTAT ATGATCTATA     2760
AATCGGGGGG GGAAG                                                     2775
```